US012778554B2

(12) United States Patent
Kano

(10) Patent No.: US 12,778,554 B2
(45) Date of Patent: Nov. 3, 2026

(54) MEDICAL IMAGE DIAGNOSIS DEVICE AND MEDICAL IMAGE DIAGNOSIS SYSTEM

(71) Applicant: Canon Kabushiki Kaisha, Tokyo (JP)

(72) Inventor: Yusuke Kano, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 230 days.

(21) Appl. No.: 18/411,539

(22) Filed: Jan. 12, 2024

(65) Prior Publication Data

US 2024/0237969 A1 Jul. 18, 2024

(30) Foreign Application Priority Data

Jan. 17, 2023 (JP) ................................ 2023-004826

(51) Int. Cl.
*A61B 8/00* (2006.01)

(52) U.S. Cl.
CPC ............ *A61B 8/462* (2013.01); *A61B 8/4245* (2013.01); *A61B 8/463* (2013.01)

(58) Field of Classification Search
CPC ......... A61B 8/12; A61B 8/4245; A61B 8/462; A61B 8/463; A61B 8/488; A61B 8/54
See application file for complete search history.

(56) References Cited

U.S. PATENT DOCUMENTS

2004/0019270 A1* 1/2004 Takeuchi ................. A61B 8/14 600/407
2014/0171959 A1* 6/2014 Yacono .............. G02B 21/0012 606/128
2020/0214680 A1* 7/2020 Miyachi ............... A61B 8/0858
2022/0133281 A1* 5/2022 Hattori ................... A61B 8/462 600/440
2023/0172583 A1* 6/2023 Ebata ................... A61B 8/4245 600/437
2024/0161907 A1* 5/2024 Jung ....................... G06T 11/00

FOREIGN PATENT DOCUMENTS

JP 2014-221175 A 11/2014

* cited by examiner

*Primary Examiner* — Brooke Lyn Klein
(74) *Attorney, Agent, or Firm* — Oblon, McClelland, Maier & Neustadt, L.L.P.

(57) ABSTRACT

According to an embodiment, a medical image diagnosis device includes processing circuitry. The processing circuitry acquires at least a reflected wave signal obtained by reflecting an ultrasound signal detected by an ultrasound probe and transmitted to a subject within a body of the subject and an image signal including an external appearance of the subject captured by an imaging device, controls a process of displaying an ultrasound image based on the reflected wave signal and a visual field image based on the image signal on a display device attached to a head of an examiner, and determines whether or not a state is an imaging state in which the ultrasound probe detects the reflected wave signal and the inside of the body of the subject is imaged. The processing circuitry dynamically changes the ratio between the size of an ultrasound image display region where the ultrasound image is displayed on the display device and the size of a visual field image display region where the visual field image is displayed on the display device based on an imaging state.

9 Claims, 8 Drawing Sheets

MEDICAL IMAGE DIAGNOSIS DEVICE AND MEDICAL IMAGE DIAGNOSIS SYSTEM

CROSS-REFERENCE TO RELATED APPLICATION

The present application claims priority based on Japanese Patent Application No. 2023-004826, filed Jan. 17, 2023, the content of which is incorporated herein by reference.

FIELD

Embodiments disclosed herein and drawings relate to a medical image diagnosis device and a medical image diagnosis system.

BACKGROUND

Conventionally, for example, an ultrasound diagnosis device has been used as a medical image diagnosis device for performing an ultrasound examination. In the ultrasound examination, an examiner needs to perform the examination while confirming both a screen of a display device provided in the ultrasound diagnosis device and a subject. For this reason, the examiner during the examination is forced to take an unreasonable orientation in order to direct his/her eyes to both the screen of the display device and the subject.

In this regard, conventionally, technology related to an ultrasound diagnosis system in which the external appearance of a living body is imaged and an ultrasound image for display is superimposed on a biological image for display and displayed on a video see-through head-mounted display has been proposed. By employing this technology, in the conventional ultrasound diagnosis system, an ultrasound image for display can be displayed as if it were being projected onto the body surface of a living body. Thereby, in the conventional ultrasound diagnosis system, the examiner does not need to direct his/her eyes to the screen of the display device provided in the ultrasound diagnosis device and the examiner does not have to take an unreasonable orientation during the examination. However, because the ultrasound image for display superimposed on the biological image for display in the conventional ultrasound diagnosis system is generated for display, the resolution necessary for the examination has not been obtained. For this reason, it is difficult to perform clinical diagnosis (determination) on the basis of the ultrasound image for display projected onto the body surface of a living body in the conventional ultrasound diagnosis system. Furthermore, when the ultrasound image for display is projected onto the body surface of the living body, it is difficult to confirm the state of a portion on which the ultrasound image for display is superimposed. For this reason, in the conventional ultrasound diagnosis system, a scanning process of the ultrasound probe on the body surface of the living body for acquiring an ultrasound image may be difficult.

DETAILED DESCRIPTION

According to an embodiment, a medical image diagnosis device includes processing circuitry. The processing circuitry acquires at least a reflected wave signal obtained by reflecting an ultrasound signal detected by an ultrasound probe and transmitted to a subject within the body of the subject and an image signal including an external appearance of the subject captured by an imaging device, controls a process of displaying an ultrasound image based on the reflected wave signal and a visual field image based on the image signal on a display device attached to the head of an examiner, and determines whether or not a state is an imaging state in which the ultrasound probe detects the reflected wave signal and the inside of the body of the subject is imaged. The processing circuitry dynamically changes the ratio between the size of an ultrasound image display region where the ultrasound image is displayed on the display device and the size of a visual field image display region where the visual field image is displayed on the display device based on an imaging state determination result.

Hereinafter, a medical image diagnosis device and a medical image diagnosis system according to embodiments will be described with reference to the drawings. For example, the medical image diagnosis device is an ultrasound diagnosis device that performs an ultrasound examination process on a subject (a patient) by transmitting an ultrasound signal from an ultrasound probe and detecting the ultrasound signal (a reflected wave signal: an echo signal) returned when the ultrasound signal is reflected inside of the body of the subject with the ultrasound probe. The medical image diagnosis device performs image processing on the reflected wave signal detected by the ultrasound probe, generates an ultrasound image based on the magnitude of the reflected wave signal and the like, and presents the generated ultrasound image to an examiner (such as a physician) of the ultrasound examination process. Thereby, the examiner can visually confirm the state of the tissue inside of the body of the subject.

Figure 1:
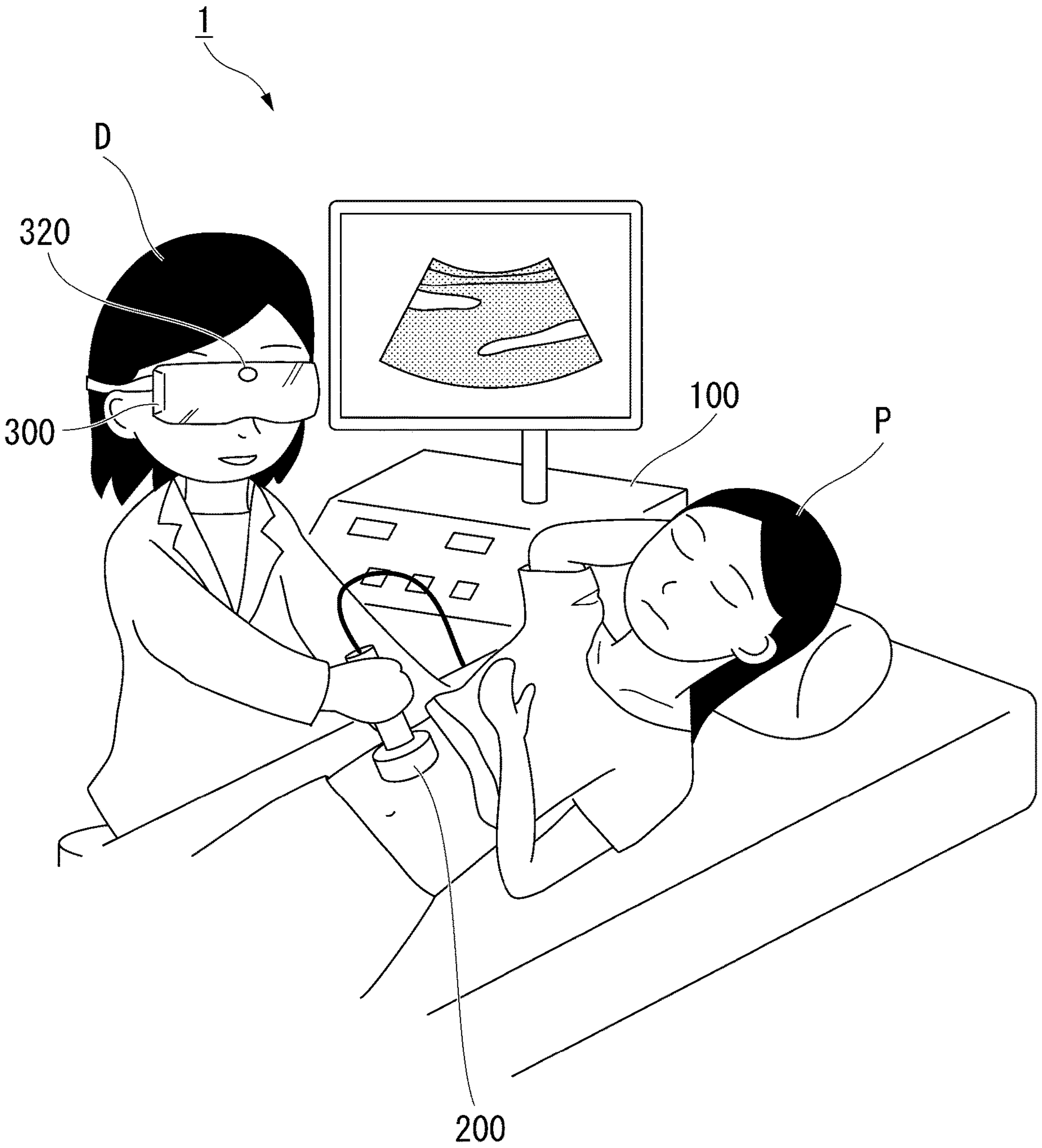
FIG. 1 is a diagram showing an example of a configuration and usage environment of a medical image diagnosis system to which a medical image diagnosis device according to an embodiment is applied.

FIG. 1 is a diagram showing an example of a configuration and usage environment of the medical image diagnosis system to which the medical image diagnosis device according to an embodiment is applied. The medical image diagnosis system 1 includes, for example, a medical image diagnosis device 100, an ultrasound probe 200, and a head-mounted display (HMD) 300.

The ultrasound probe 200 is used in contact with or in proximity to the body surface of the subject P. The ultrasound probe 200 transmits (emits) a directional ultrasound signal to the body of the subject P in accordance with control from the medical image diagnosis device 100, detects the reflected wave signal reflected inside of the body of the subject P, and outputs the reflected wave signal to the medical image diagnosis device 100. The ultrasound probe 200 includes a plurality of ultrasound transducers. The ultrasound transducers are, for example, piezoelectric elements such as piezoelectric ceramics. The ultrasound probe 200 further includes a matching layer provided on each of the ultrasound transducers, a backing material that prevents the ultrasound signal from propagating to the rear of the ultrasound transducer (to the opposite side of the subject P), and the like. The plurality of ultrasound transducers are arranged inside of the ultrasound probe 200 in any arrangement method such as a single row or a two-dimensional arrangement. The ultrasound probe 200 may be detachable from the medical image diagnosis device 100. The ultrasound probe 200 and the medical image diagnosis device 100 may be connected by a dedicated cable or may be connected using a wireless communication function.

The ultrasound probe 200 may be configured to include, for example, a magnetic sensor, in addition to a general configuration for transmitting an ultrasound signal and detecting a reflected wave signal or may be configured to be separately attached. In this case, on the basis of detection results of the magnetic sensor, it is possible to determine changes in the position and orientation of the ultrasound probe 200, i.e., a position on the body surface of the subject P in a horizontal direction, a position and angle for the body surface in a vertical direction, and the like.

The HMD 300 is used while attached to the head of the examiner D to cover the eyes. The HMD 300 is a video-transmissive head-mounted display. The HMD 300 includes, for example, at least a camera 320 and a display 340 (not shown). The camera 320 is, for example, a digital camera using a solid-state imaging device such as a charge-coupled device (CCD) or a complementary metal-oxide-semiconductor (CMOS). The camera 320 is attached to any location on the HMD 300. For example, the camera 320 is attached to the position of the center of the HMD 300 or the like. For example, the camera 320 periodically and repeatedly images a range of the visual field of the examiner D and outputs an image signal indicating the captured image. The camera 320 may be a stereo camera. The HMD 300 transmits (transfers) an image signal output by the camera 320 to the medical image diagnosis device 100. The display 340 (not shown) is, for example, a display device such as a liquid crystal display (LCD) or an organic electroluminescence (EL) display. The display 340 is arranged in front of the eyes of the examiner D. The display 340 may include one display device in total or may include two display devices corresponding to the left eye and right eye of the examiner D. The display 340 displays the display image transmitted by the medical image diagnosis device 100. For example, the display 340 displays a display image based on an image signal captured by the camera 320 and transmitted by the medical image diagnosis device 100, thereby allowing the examiner D whose eyes are covered to recognize the state of the visual field range. For example, the display 340 can allow the examiner D to confirm (diagnose) the state of the inside of the body of the subject P by displaying a display image based on the reflected wave signal transmitted by the medical image diagnosis device 100 and detected by the ultrasound probe 200 from the inside of the body of the subject P. The HMD 300 and medical image diagnosis device 100 may be connected by a dedicated cable or using a wireless communication function.

The camera 320 is an example of an "imaging device" and the display 340 is an example of a "display device."

The HMD 300 may be configured to include, for example, a visual line sensor, in addition to a general configuration for causing the display 340 to display a display image based on an image signal obtained in an imaging process of the camera 320. In this case, it is possible to determine a direction of the visual line of the examiner D wearing the HMD 300, a position of the visual line within an angle of view of the display image displayed on the display 340, or the like on the basis of a detection result of the visual line sensor.

The medical image diagnosis device 100 causes the ultrasound probe 200 to transmit (emit) an ultrasound signal and generates an ultrasound image on the basis of a reflected wave signal detected and output by the ultrasound probe 200. The medical image diagnosis device 100 generates an image within the range of the visual field of the examiner D on the basis of an image signal transmitted (transferred) by the HMD 300 and obtained in an imaging process of the camera 320. In the following description, it is assumed that the medical image diagnosis device 100 generates, for example, an image (hereinafter referred to as a "visual field image") including the external appearance of the subject P visible in the range of the visual field of the examiner D who is performing an ultrasound examination process on the subject P. The medical image diagnosis device 100 transmits a display image including both or one of the generated ultrasound image and the generated visual field image to the HMD 300 and causes the display 340 to display the display image. Thereby, the medical image diagnosis device 100 allows the examiner D to confirm both the visual field image and the ultrasound image. In other words, the medical image diagnosis device 100 allows the examiner D to smoothly confirm both the state of the external appearance of the subject P and the state of the inside of the body of the subject P.

Configuration of Medical Image Diagnosis Device

Figure 2:
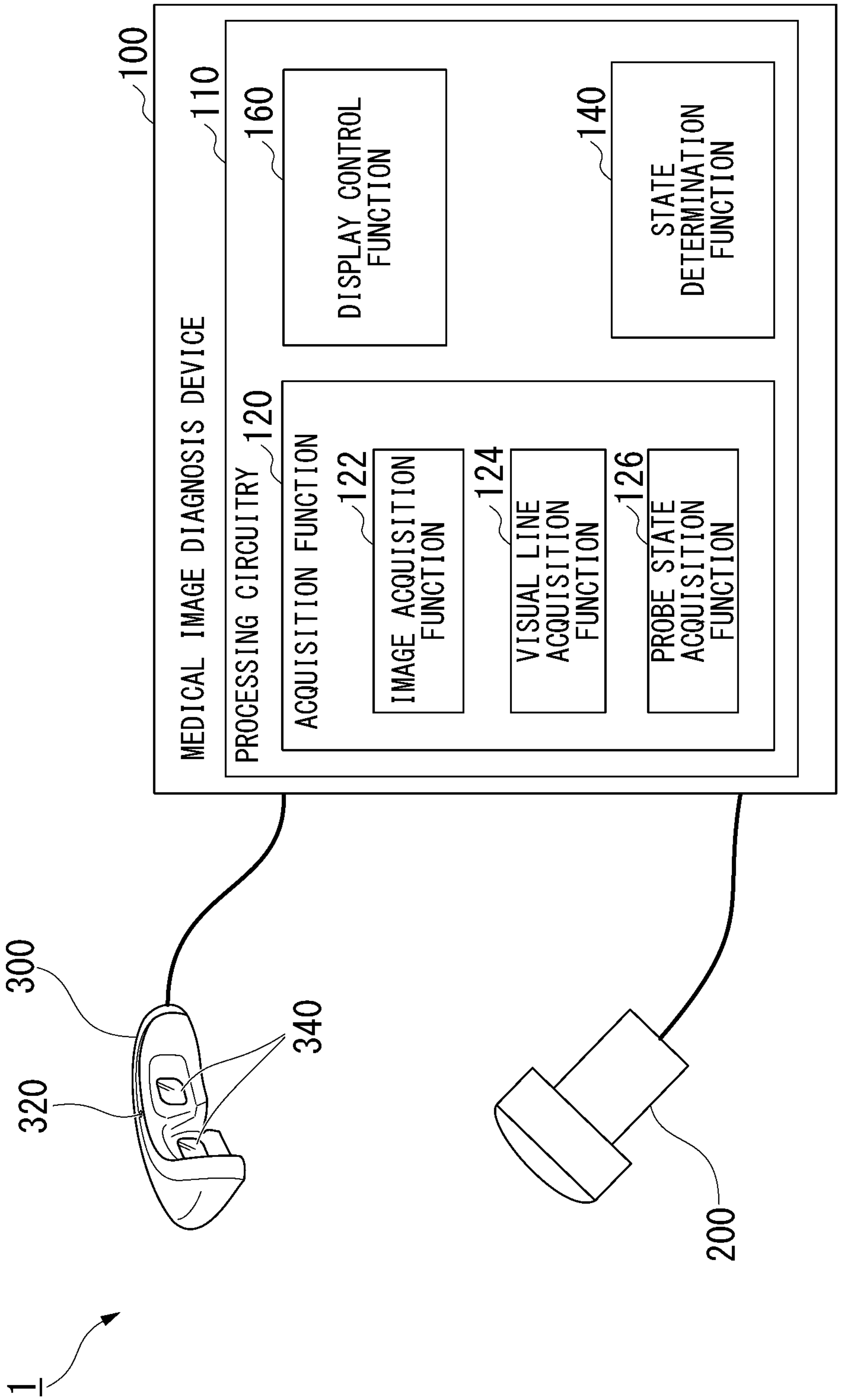
FIG. 2 is a diagram showing an example of a functional configuration of the medical image diagnosis device according to the embodiment.

FIG. 2 is a diagram showing an example of the functional configuration of the medical image diagnosis device 100 according to the embodiment. The medical image diagnosis device 100 includes, for example, processing circuitry 110. In FIG. 2, an example of a functional configuration of the processing circuitry 110 in the medical image diagnosis device 100 for implementing the function of displaying a display image on the display 340 provided in the HMD 300 is shown. Furthermore, in FIG. 2, an example of the ultrasound probe 200 and the HMD 300 connected to the medical image diagnosis device 100 as the medical image diagnosis system 1 is also shown.

On the other hand, the illustration of other components and functional configurations not related to the display of display images in the medical image diagnosis device 100 is omitted from FIG. 2. For example, the illustration of input/output circuitry configured to output a control signal for causing the ultrasound probe 200 to transmit (emit) an ultrasound signal and receive a reflected wave signal output by the ultrasound probe 200 and input/output circuitry for receiving an image signal transmitted (transferred) by the HMD 300 and outputting a display image to be displayed on the HMD 300 is omitted from FIG. 2. For example, the illustration of image processing circuitry (an image processing function) for generating an ultrasound image based on a reflected wave signal output by the ultrasound probe 200 or for generating a visual field image based on an image signal transmitted (transferred) by the HMD 300 is omitted from FIG. 2. For example, the illustration of control circuitry (a control function) for controlling the entire operation of the medical image diagnosis device 100 or the medical image diagnosis system 1 or operation circuitry (an operation function) for operating the medical image diagnosis device 100 when the examiner D performs an ultrasound examination process, i.e., the input/output interface, is omitted from FIG. 2. It is only necessary for the configurations and operations of these omitted components and functional configurations to be equivalent to the configurations and operations of the components and functional configurations provided in existing ultrasound diagnosis devices. Therefore, a detailed description of the configurations and operations of the omitted components and functional configurations will be omitted.

The processing circuitry 110, for example, executes processes of an acquisition function 120, a state determination function 140, a display control function 160, and the like. The acquisition function 120, for example, is performed to execute processes of an image acquisition function 122, a visual line acquisition function 124, a probe state acquisition function 126, and the like. The processing circuitry 110, for example, implements these functions when a hardware processor executes a program (software) stored in a memory (not shown). The memory (not shown) is implemented by, for example, a read-only memory (ROM), a random-access memory (RAM), a semiconductor memory element such as a flash memory, a hard disk drive (HDD), an optical disc, or the like.

The hardware processor is, for example, circuitry such as a central processing unit (CPU), a graphics processing unit (GPU), an application-specific integrated circuit (ASIC), or a programmable logic device (for example, a simple programmable logic device (SPLD), a complex programmable logic device (CPLD), or a field programmable gate array (FPGA)). Instead of storing the program in the memory (not shown), the program may be directly embedded in the circuitry of the hardware processor. In this case, the hardware processor implements each function by reading and executing the program embedded in the circuitry. The hardware processor is not limited to being configured as single circuitry and may be configured as one hardware processor by combining a plurality of independent circuits to implement each function. A plurality of components may be integrated into one hardware processor to implement each function. Each function may be implemented by incorporating a plurality of components into one dedicated LSI circuit. Here, the program (software) may be stored in advance in a storage device (a storage device having a non-transitory storage medium) that constitutes a semiconductor memory device such as a ROM, a RAM, or a flash memory or a storage device such as a hard disk drive. Alternatively, the program (software) may be stored in a removable storage medium (a non-transitory storage medium) such as a DVD or CD-ROM and installed in a storage device (not shown) provided in the medical image diagnosis device 100 when the storage medium is mounted in a drive device provided in the medical image diagnosis device 100. The program (software) may be downloaded in advance from another computer device via a network (not shown) and installed in the storage device provided in the medical image diagnosis device 100. A program (software) installed in the storage device (not shown) provided in the medical image diagnosis device 100 may be transferred to a storage device (not shown) provided in the processing circuitry 110 and executed.

The acquisition function 120 is performed to acquire various information in ultrasound examinations. The acquisition function 120 is an example of an "acquirer."

The image acquisition function 122 is performed to acquire the reflected wave signal output by the ultrasound probe 200. The image acquisition function 122 is performed to output the acquired reflected wave signal to the state determination function 140. The image acquisition function 122 is performed to acquire an image signal transmitted (transferred) by the HMD 300.

The image acquisition function 122 is performed to output the acquired reflected wave signal and the acquired image signal to the image processing circuitry (the image processing function) (not shown). Thereby, in the medical image diagnosis device 100, the image processing circuitry (the image processing function) (not shown) generates an ultrasound image based on the reflected wave signal output by the ultrasound probe 200, and a visual field image based on an image signal transmitted (transferred) by the HMD 300. The image acquisition function 122 may be performed to generate an ultrasound image on the basis of the acquired reflected wave signal and may be performed to generate a visual field image on the basis of the acquired image signal. In this case, the image acquisition function 122 may be performed to output the generated ultrasound image to the state determination function 140. In the processing circuitry 110, the ultrasound image and the visual field image generated by the image processing circuitry (the image processing function) (not shown) or the image acquisition function 122 are output to the display control function 160.

For example, when the HMD 300 is configured to include a visual line sensor, the visual line acquisition function 124 is performed to acquire the detection result of the visual line sensor, i.e., information indicating a direction of the visual line of the examiner D wearing the HMD 300 or a position of a visual line of the examiner D within the angle of view of the display image displayed on the display 340 provided in the HMD 300 (hereinafter referred to as "visual line information"). The visual line acquisition function 124 is performed to output the acquired visual line information to the state determination function 140. When the HMD 300 does not include a visual line sensor, the visual line acquisition function 124 may be omitted.

For example, when the ultrasound probe 200 includes a magnetic sensor or has a configuration that can be separately attached, the probe state acquisition function 126 acquires the detection result of the magnetic sensor, i.e., information indicating a position and orientation when the ultrasound probe 200 detects a reflected wave signal (a change in a position on the body surface of the subject P in a horizontal direction or a position or an angle for the body surface in a vertical direction) (hereinafter referred to as "probe state information"). The visual line acquisition function 124 is performed to output the acquired probe state information to the state determination function 140. When the ultrasound probe 200 does not include a magnetic sensor or has a configuration that cannot be separately attached, the probe state acquisition function 126 may be omitted.

The state determination function 140 is performed to determine the state of the ultrasound examination being performed in the medical image diagnosis device 100. More specifically, the state determination function 140 is performed to determine whether or not the state is a state in which the ultrasound probe 200 is detecting a reflected wave signal reflected inside of the body of the subject P, in other words, a state in which the ultrasound probe 200 is imaging the inside of the body of the subject P (hereinafter referred to as an “imaging state”) on the basis of the reflected wave signal output by the image acquisition function 122. At this time, the state determination function 140 is performed to determine the imaging state using a difference between a value of the reflected wave signal detected when the ultrasound probe 200 is in contact with or in proximity to the body surface of the subject P and a value of the reflected wave signal detected when the ultrasound probe 200 is away from the body surface of the subject P (the ultrasound probe 200 is in the air), i.e., a change in the value of the reflected wave signal. At this time, the state determination function 140 may be performed to determine the imaging state, for example, using a value obtained by adding or averaging all values of reflected wave signals or values within a prescribed range detected by the ultrasound probe 200 as a value of a reflected wave signal. Here, the value of the reflected wave signal corresponds to a pixel value in an ultrasound image generated on the basis of the reflected wave signal. Therefore, the state determination function 140 is performed to determine the imaging state using a difference between the pixel value of the ultrasound image when the ultrasound probe 200 is in contact with or in proximity to the body surface of the subject P and the pixel value of the ultrasound image when the ultrasound probe 200 is in the air. In the following description, the value of the reflected wave signal is also simply referred to as a “pixel value.” For example, the pixel value when the ultrasound probe 200 is in contact with or in proximity to the body surface of the subject P indicates the inside of the body of the subject P and therefore is a pixel value differing according to each location. Furthermore, a pixel value of the case where the ultrasound probe 200 is moving in a state in which it is in contact with or in proximity to the body surface of the subject P, i.e., the case where the examiner D scans the ultrasound probe 200 to search for a portion inside of the body of the subject P on which an ultrasound examination process is performed, is a pixel value that differs according to the location and, furthermore, the pixel value changes greatly within a certain period of time. On the other hand, when the ultrasound probe 200 is in the air, the pixel values do not differ for each location, but are entirely similar pixel values, the values do not change, or the change is significantly small even if the values change. For example, the pixel value when the ultrasound probe 200 is in the air is a characteristic value indicating that the ultrasound image is entirely black (completely black). The state determination function 140 is performed to determine the imaging state in the ultrasound probe 200 according to whether or not the value of the reflected wave signal output by the image acquisition function 122 is a characteristic value of the case where the ultrasound probe 200 is in the air (a pixel value indicating that the ultrasound image is entirely black). Furthermore, the state determination function 140 is performed to determine whether the state is an imaging state in which the examiner D performs a scan process with the ultrasound probe 200 or an imaging state in which the ultrasound probe 200 is fixed to a specific location for the examiner D to diagnose a portion inside of the body of the subject P according to whether or not the value of the reflected wave signal significantly changes within a fixed period of time when the value of the reflected wave signal output by the image acquisition function 122 is a value of the state in which the ultrasound probe 200 is in contact with or in proximity to the body surface of the subject P (a pixel value differing according to each location).

When the probe state acquisition function 126 is performed to output probe state information, the state determination function 140 may be performed to determine the imaging state on the basis of the probe state information. At this time, the state determination function 140 is performed to determine the imaging state using changes in the position and orientation of the ultrasound probe 200 indicated in the probe state information. For example, when the ultrasound probe 200 is in contact with or in proximity to the body surface of the subject P, the change in the position of the ultrasound probe 200 indicated in the probe state information is significantly small even if the position on the body surface of the subject P in the vertical direction is constant or is not constant. Furthermore, when the ultrasound probe 200 is moving in contact with or in proximity to the body surface of the subject P (when the examiner D is performing the scan process with the ultrasound probe 200), the position on the body surface of the subject P in the horizontal direction significantly changes within a certain period of time as the position of the ultrasound probe 200 indicated in the probe state information. On the other hand, when the ultrasound probe 200 is in the air, the position of the ultrasound probe 200 indicated in the probe state information changes significantly in the vertical and horizontal directions. The state determination function 140 is performed to determine the imaging state in the ultrasound probe 200 according to whether or not the change in the position of the ultrasound probe 200 indicated in the probe state information is a characteristic change (a large change in the vertical and horizontal directions) when the ultrasound probe 200 is in the air. Furthermore, when the position of the ultrasound probe 200 indicated in the probe state information is a position where the ultrasound probe 200 is in contact with or in proximity to the body surface of the subject P, the state determination function 140 is performed to determine whether the state is an imaging state in which the examiner D performs a scan process with the ultrasound probe 200 or an imaging state in which the ultrasound probe 200 is fixed to a specific location for the examiner D to diagnose a portion inside of the body of the subject P according to whether the position in the horizontal direction changes significantly within a certain period of time. The probe state information is an example of a “detection position of a reflected wave signal.” The imaging state determined by the state determination function 140 on the basis of the probe state information is an example of a “detection state in the ultrasound probe.”

The determination of the imaging state in the state determination function 140 is not limited to the determination based on a value of a reflected wave signal (a pixel value) or a probe state information. For example, the state determination function 140 may be performed to determine the imaging state on the basis of the position of the ultrasound probe 200 imaged in the visual field image. Furthermore, the determination of the imaging state in the state determination function 140 is not limited to the determination of whether the state is an imaging state in which the ultrasound probe 200 is fixed in contact with or in proximity to the body surface of the subject P, an imaging state in which the examiner D performs a scan process with the ultrasound probe 200 in contact with or in proximity to the body surface of the subject P, or a state in which the ultrasound probe 200 is in the air. For example, the state determination function 140 may be performed to determine a period of time that elapses after the ultrasound probe 200 is fixed, a speed of movement of the ultrasound probe 200 during scanning, or the like as the imaging state.

The state determination function 140 is performed to output at least information indicating a determination result of determining that the state is an imaging state in which the ultrasound probe 200 is in contact with or in proximity to the body surface of the subject P or a state in which the ultrasound probe 200 is away from the body surface of the subject P (the ultrasound probe 200 is in the air) (hereinafter referred to as an "imaging state determination result") to the display control function 160. When it is determined that the state is an imaging state in which the ultrasound probe 200 is in contact with or in proximity to the body surface of the subject P, the state determination function 140 may be performed to output the imaging state determination result indicating the determination result of determining whether the state is an imaging state in which the ultrasound probe 200 is fixed or an imaging state in which the examiner D performs a scan process with the ultrasound probe 200 to the display control function 160.

Furthermore, the state determination function 140 is performed to determine which position of a display region of a display image of the display 340 provided in the HMD 300 is being gazed at by the examiner D (hereinafter referred to as a "gaze state") on the basis of visual line information output in the visual line acquisition function 124. For example, the state determination function 140 is performed to determine that the examiner D is gazing at the position of the visual line when the position of the visual line of the examiner D indicated in the visual line information is continuously fixed at the same position for a prescribed period of time or longer and determine that the examiner D is not gazing at the position of the visual line when the position of the visual line of the examiner D is not fixed. Thereby, for example, when both an ultrasound image and a visual field image are displayed on the display 340 included in the HMD 300, the state determination function 140 can be performed to determine which of the ultrasound image and the visual field image is being gazed at by the examiner D. The state determination function 140 is performed to output information indicating the determination result of determining the gaze state of the examiner D (hereinafter referred to as a "gaze state determination result") to the display control function 160.

The display control function 160 is performed to control the display of display images on the display 340 provided in the HMD 300. More specifically, the display control function 160 is performed to generate a display image for displaying both or one of an ultrasound image and a visual field image on the display 340, transmit the generated display image to the HMD 300, and cause the display 340 to display the display image. At this time, the display control function 160 is performed to dynamically change the size of a display region of an ultrasound image (hereinafter referred to as an "ultrasound image display region") to be displayed on the display 340 on the basis of the imaging state determination result output in the state determination function 140 and the size of a display region of a visual field image to be displayed on the display 340 (hereinafter referred to as a "visual field image display region"), generate a display image in which images corresponding to the display regions are arranged, and cause the display 340 to display the display image. That is, the display control function 160 is performed to dynamically change the ratio between the size of the ultrasound image superimposed as a display image and the size of the visual field image and cause the display 340 to display the image.

Figure 3:
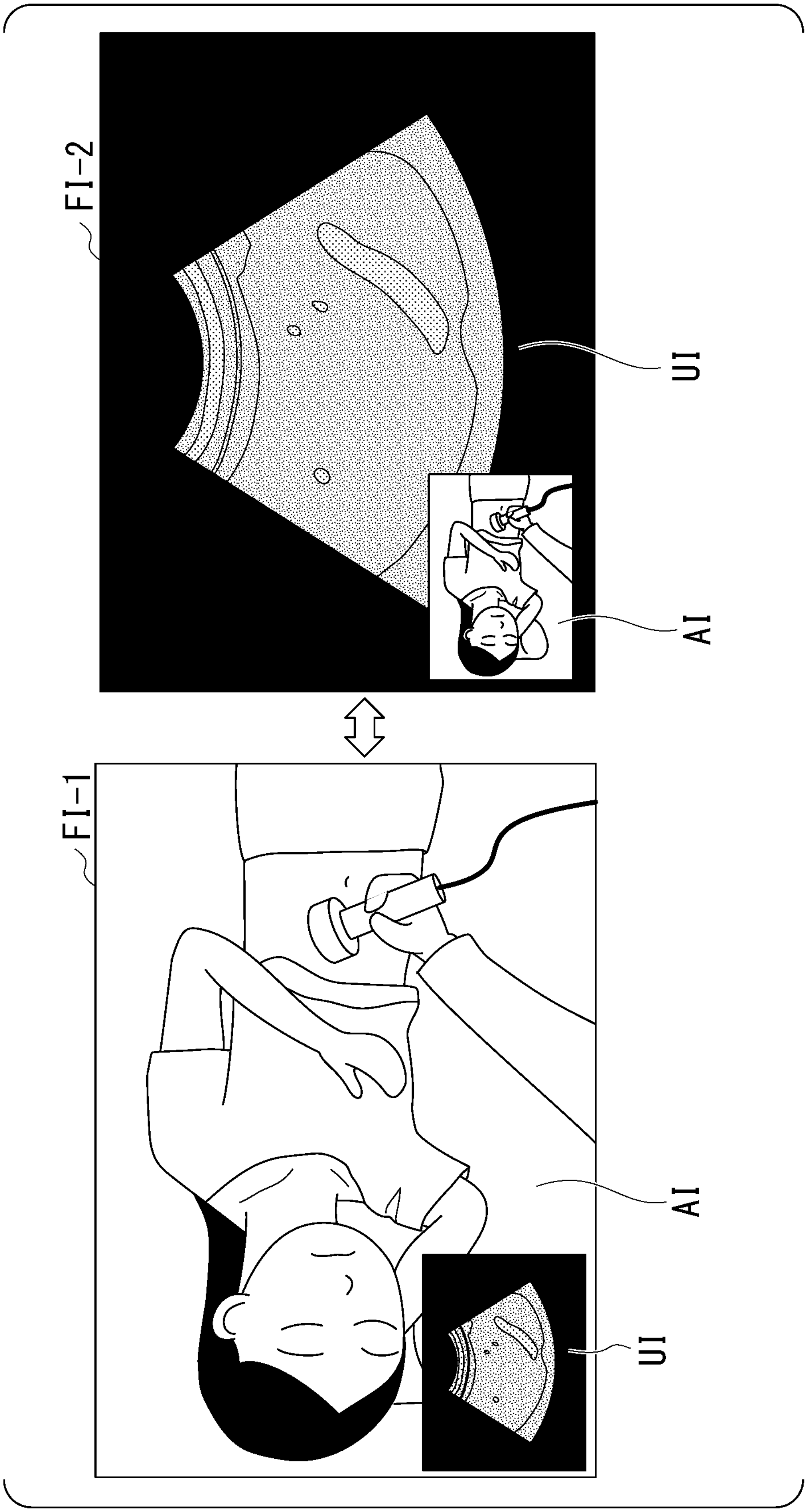
FIG. 3 is a diagram showing an example of a display image displayed on a display device by the medical image diagnosis device according to the embodiment.

Here, an example of a display image generated in the display control function 160 and displayed on the display 340 will be described. FIG. 3 is a diagram showing an example of a display image displayed on the display device (the display 340) by the medical image diagnosis device 100 according to the embodiment. FIG. 3 shows an example of a display image for displaying both an ultrasound image and a visual field image on the display 340.

In FIG. 3, a display image FI-1 is an example of a display image when a visual field image display region where a visual field image AI is displayed is enlarged and the ultrasound image display region where an ultrasound image UI is displayed is reduced. For example, when the ultrasound probe 200 is away from the body surface of the subject P (the ultrasound probe 200 is in the air), the display control function 160 is performed to generate the display image FI-1 by superimposing the ultrasound image UI on the visual field image AI and cause the display 340 to display the display image FI-1. Using the display image FI-1, the examiner D can mainly confirm the visual field image AI including the external appearance of the subject P when the ultrasound probe 200 does not come into contact with the subject P. A state in which the ultrasound probe 200 is away from the body surface of the subject P (the ultrasound probe 200 is in the air) is an example of a "first state."

In FIG. 3, a display image FI-2 is an example of a display image of the case where an ultrasound image display region where the ultrasound image UI is displayed is enlarged and a visual field image display region where the visual field image AI is displayed is reduced. For example, when the ultrasound probe 200 is in contact with the body surface of the subject P, the display control function 160 is performed to generate the display image FI-2 by superimposing the visual field image AI on the ultrasound image UI and causes the display 340 to display the display image FI-2. When the examiner D can scan the ultrasound probe 200 to search for a portion inside of the body of the subject P who will undergo an ultrasound examination using the display image FI-2 or when the ultrasound probe 200 is fixed at a specific location for diagnosis of the portion inside of the body of the subject P, it is possible to mainly confirm the ultrasound image UI of the inside of the body of the subject P. The state in which the ultrasound probe 200 is in contact with the body surface of the subject P is an example of a "second state."

The display control function 160 is performed to cause the examiner D to perform both the confirmation of the visual field image AI and the confirmation of the ultrasound image UI by dynamically changing the size of the ultrasound image display region and the size of the visual field image display region on the basis of the imaging state determination result (more specifically, the display control function 160 is performed to dynamically switch displaying between displaying of the display image FI-1 on the display 340 and displaying of the display image FI-2 on the display 340). The dynamic switching between displaying the display image FI-1 on the display 340 and displaying the display image FI-2 on the display 340 in the display control function 160 is not limited to dynamic switching based on the imaging state determination result, but may be performed on the basis of the gaze state determination result output in the state determination function 140. More specifically, the display control function 160 may be performed to cause the display 340 to display the display image FI-1 when the gaze state determination result indicates a state in which the examiner D is gazing at the visual field image AI and cause the display 340 to display the display image FI-2 when the gaze state determination result indicates a state in which the examiner D is gazing at the ultrasound image UI. Furthermore, when the gaze state determination result indicates a state in which the examiner D is continuously gazing at one image for a predetermined period of time or longer, the display control function 160, for example, may be performed to cause the display 340 to display an enlarged image by enlarging the image at which the examiner D is gazing by designating the position where the visual line of the examiner D is fixed as the center. The magnification rate of the image at this time may be a prescribed magnification rate or the magnification rate may be increased according to how long the examiner D is gazing (so-called zooming).

Although an example in which the display image FI-1 is displayed when the ultrasound probe 200 is in the air and the display image FI-2 is displayed when the ultrasound probe 200 is in contact with the body surface of the subject P has been described with reference to FIG. 3, the switching of the display image FI to be displayed on the display 340 is not limited to the above-described example. For example, the display control function 160 may be performed to generate a display image FI of only the visual field image AI and cause the display 340 to display the display image FI when the ultrasound probe 200 is in the air before the examiner D performs an ultrasound examination or the like. In this case, the display control function 160 may be performed to generate the display image FI-1 and cause the display 340 to display the display image FI-1 when the ultrasound probe 200 is scanned to search for a portion inside of the body of the subject P and may be performed to generate the display image FI-2 and cause the display 340 to display the display image FI-2 when the ultrasound probe 200 is fixed at a specific location on the body surface of the subject P. Thereby, the examiner D can search for the portion inside of the body of the subject P by scanning the ultrasound probe 200 while easily confirming the ultrasound image UI with the display image FI-1 and can confirm the ultrasound image UI in detail with the display image FI-2 and perform clinical diagnosis (determination) when the ultrasound probe 200 is fixed to a specific location for a diagnosis process of the examiner D.

Furthermore, although an example of the display image FI in which one of the visual field image AI and the ultrasound image UI is superimposed on the other image is shown in FIG. 3, the display image FI is not limited to a configuration in which the images are superimposed. For example, a configuration in which the display region is divided (divided into two) at any position within the display image FI, the visual field image AI is placed in one display region, and the ultrasound image UI is placed in the other display region may be adopted. In this case as well, the display control function 160 is performed to dynamically change the size of the display region (visual field image display region) where the visual field image AI is placed and the display region (ultrasound image display region) where the ultrasound image UI is placed on the basis of the imaging state determination result.

With such a configuration, the medical image diagnosis device 100 causes the display 340 provided in the HMD 300 to display both the visual field image captured by the camera 320 provided in the HMD 300 and the ultrasound image captured by the ultrasound probe 200. In other words, the medical image diagnosis device 100 allows both the visual field image and the ultrasound image to fall within the visual field of the examiner D at the same time. Thereby, the examiner D who performs an ultrasound examination using the medical image diagnosis device 100 can simultaneously confirm the visual field image and the ultrasound image within the range of the visual field without taking an unreasonable orientation. Furthermore, the medical image diagnosis device 100 dynamically changes the sizes of the visual field image and the ultrasound image displayed on the HMD 300 in accordance with the imaging state during the examination. Thereby, the examiner D who performs the ultrasound examination using the medical image diagnosis device 100 can smoothly confirm both the state of the external appearance of the subject P and the state of the inside of the body of the subject P using high-resolution images.

In the above-described configuration of the medical image diagnosis system 1, a case where the ultrasound probe 200 is used in a state in which it is in contact with or in proximity to the body surface of the subject P has been described. However, the ultrasound examinations include an ultrasound examination in which an ultrasound probe is inserted into the body of the subject P, such as a trans-esophageal echocardiography (TEE) examination. In this case, the display control function 160 may be performed to cause the display 340 to display information for assisting the examiner D in the examination. For example, the display control function 160 may be performed to cause the display 340 to display a virtual image indicating a positional relationship between an organ inside of the body of the subject P and the ultrasound probe inserted into the body, along with the visual field image and the ultrasound image.

Figure 4:
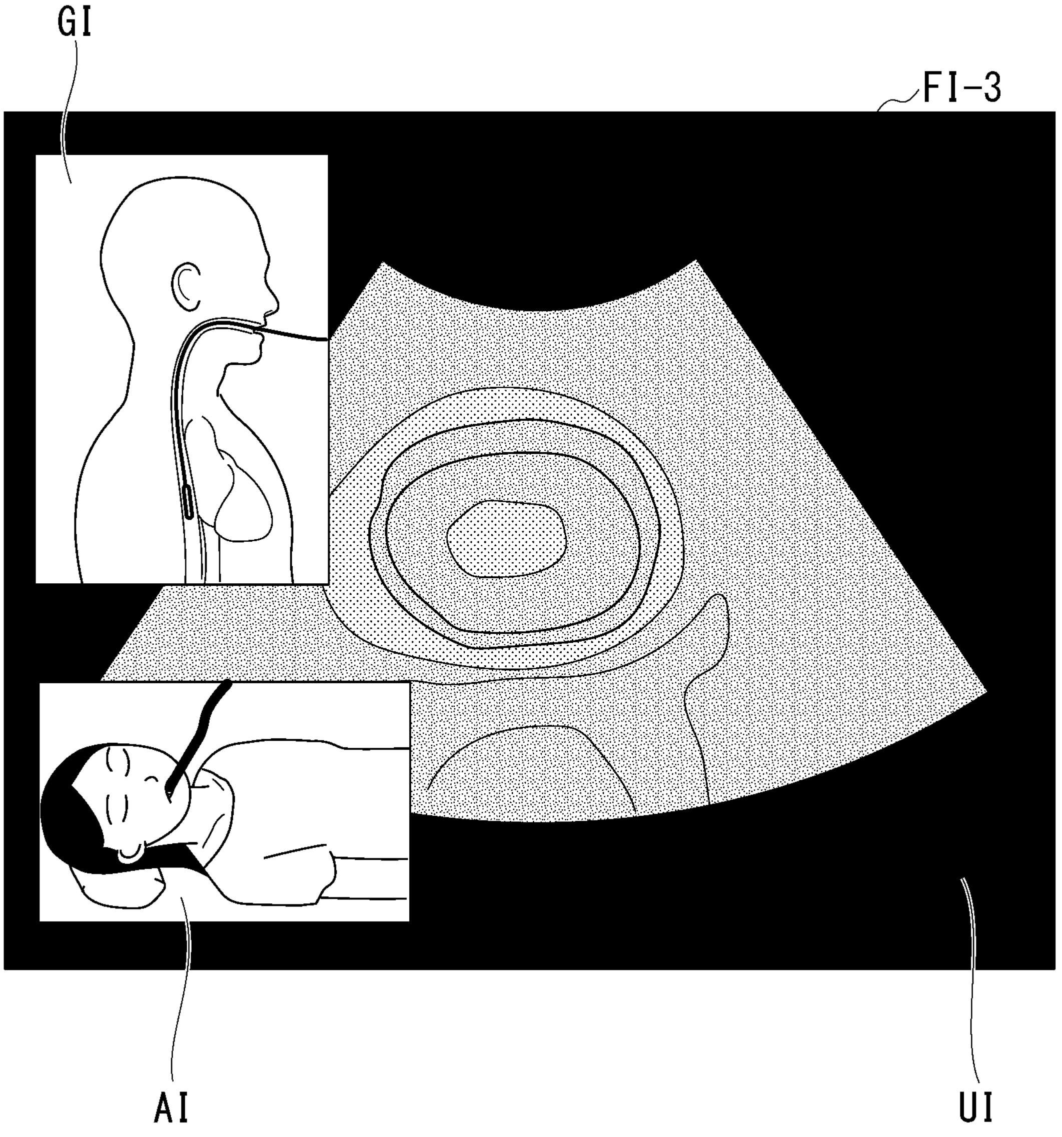
FIG. 4 is a diagram showing an example (part 1) of another display image displayed on the display device by the medical image diagnosis device according to the embodiment.

FIG. 4 is a diagram showing an example of another display image displayed on the display device (the display 340) by the medical image diagnosis device 100 according to the embodiment. In FIG. 4, an example of a display image FI-3 in which a virtual graphic image GI is displayed on the display 340 is shown in addition to both the ultrasound image UI and the visual field image AI. More specifically, an example of a display image FI-3 of the case where a graphic image GI is superimposed on the display image FI-2 shown in FIG. 3 is shown. In the graphic image GI, the current position of the inserted transesophageal ultrasound probe is shown in an in-vivo image schematically showing the esophagus and heart of the subject P. Using the display image FI-3, the examiner D can insert the transesophageal ultrasound probe into the subject P while confirming the state of the subject P using the visual field image AI, confirm the ultrasound image UI in detail while confirming the position of the transesophageal ultrasound probe using the graphic image GI, and make a clinical diagnosis (determination).

A method of indicating the current position of the transesophageal ultrasound probe inserted into the subject P is not limited to the method using the graphic image GI. For example, instead of the graphic image GI, the current position of the transesophageal ultrasound probe may be shown on the body surface of the subject P within the visual field image AI.

Furthermore, the display control function 160 may be performed to cause the display 340 to display, for example, an operation image for operating the medical image diagnosis device 100 during an ultrasound examination on the display 340 together with a visual field image and an ultrasound image as information for assisting the examiner D in performing the examination process.

Figure 5:
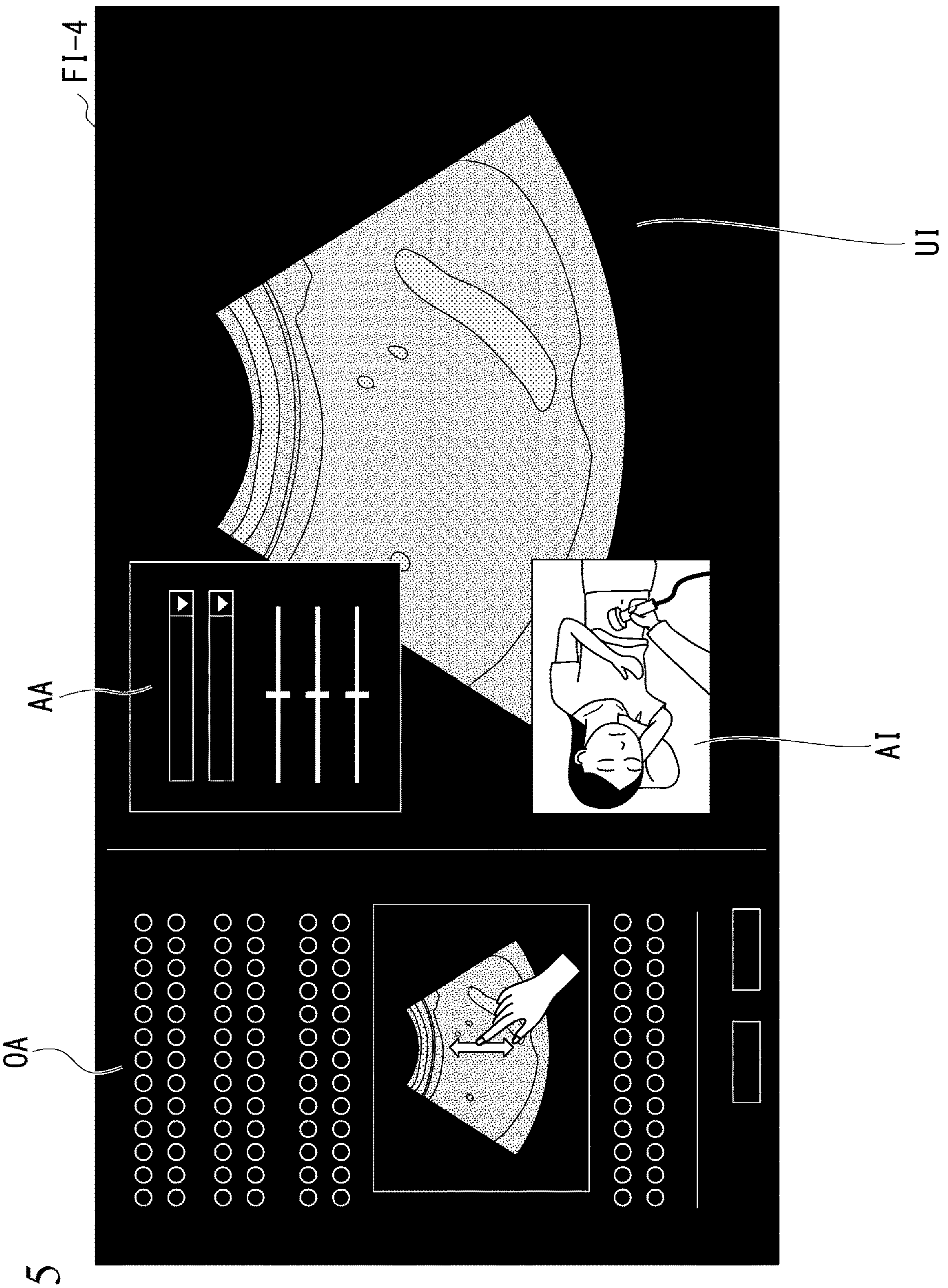
FIG. 5 is a diagram showing an example (part 2) of another display image displayed on the display device by the medical image diagnosis device according to the embodiment.

FIG. 5 is a diagram showing an example of yet another display image displayed on the display device (the display 340) by the medical image diagnosis device 100 according to the embodiment. In FIG. 5, an example of a display image FI-4 in which an operation image for operating the medical image diagnosis device 100 is displayed on the display 340 is shown in addition to both the ultrasound image UI and the visual field image AI. More specifically, the example of the display image FI-4 in which an operation image is superimposed on a display image FI-2 shown in FIG. 3 is shown. However, in the display image FI-4, a part of the operation image is shown outside of the display range(=ultrasound image display region) of the display image FI on the display 340 for ease of description. More specifically, in the operation image, an adjustment operation region AA for performing an operation for adjusting transmission of an ultrasound signal and detection of a reflected wave signal by the ultrasound probe 200 is shown within the display range and an operation guide region OA indicating an operation procedure (an operation guide) for measuring the inside of the body of the patient P imaged on the ultrasound image UI is shown outside of the display range. The adjustment operation region AA and the operation guide region OA are not limited to being displayed at the same time, but may be switched and displayed according to an operation of the examiner D. The adjustment operation performed by the examiner D on the adjustment operation region AA and the operation of switching between the adjustment operation region AA and the operation guide region OA (which may include an operation of issuing an instruction to start displaying an operation image) can be performed, for example, when the examiner D moves the visual line. For example, the examiner D may perform an operation of switching the region between the adjustment operation region AA and the operation guide region OA by moving his/her gaze of the visual line to a position of any prescribed corner among four corners of the ultrasound image display region. In this case, the display control function 160 may be performed to recognize the operation by the examiner D, for example, by using the gaze state determination result determined by the state determination function 140 on the basis of the visual line information acquired by the visual line acquisition function 124. The examiner D operates the medical image diagnosis device 100 using the operation image shown in the display image FI-4, thereby performing an operation on the medical image diagnosis device 100 necessary for the ultrasound examination while confirming the ultrasound image UI in detail.

The adjustment operation performed by the examiner D on the adjustment operation region AA and the switching operation between the adjustment operation region AA and the operation guide region OA (which may include an operation of issuing an instruction to start displaying an operation image) are not limited to the above-described operations using the visual line of the examiner D. For example, the examiner D may perform an action of moving his/her head, such as tilting his/her face or shaking his/her head. For example, the examiner D may make a prescribed movement such as operating the operation image (so-called gesture) using his/her hand or arm that is not gripping the ultrasound probe 200 within the imaging range of the camera 320 (which may be the angle of view of the camera 320) that is capturing the visual field image AI. In this case, in the processing circuitry 110, for example, it is only necessary for an image recognition function (not shown) to be performed to perform image processing including the recognition of the hands and arms of the examiner D captured in the visual field image and the determination of the movement of the recognized hands and arms and output an image processing result to the display control function 160. For example, when the HMD 300 includes a sound collection device such as a microphone, the examiner D may operate the operation image through utterance. In this case, in the processing circuitry 110, for example, it is only necessary to adopt a configuration in which the sound recognition function (not shown) is performed to perform sound processing including recognition of the collected sound of examiner D and determination of the operation indicated by the recognized sound and output its result to the display control function 160. Because the configuration and processing in these cases can be easily conceived on the basis of, for example, the configuration of the medical image diagnosis device 100 shown in FIG. 2, the above-described processes, and existing image recognition technology and sound recognition technology, a detailed description thereof will be omitted.

Configuration of Modified Example of Medical Image Diagnosis Device

Furthermore, the display control function 160 may be performed to cause the display 340 to display, for example, information indicating results of past (past) ultrasound examinations for the same subject P, as information for assisting the examiner D in performing the examination together with a visual field image or an ultrasound image in the current ultrasound examination. In this case, the information indicating the results of ultrasound examinations performed on the subject P in the past may be information stored within the medical image diagnosis device 100 or information stored in the system including another device or equipment different from the medical image diagnosis device 100. A system including other devices or equipment different from the medical image diagnosis device 100 is, for example, a database system such as a medical image archiving and communication system (picture archiving and communication systems (PACS)) that manages data of various types of medical images or an electronic medical record system that manages electronic medical records attached as information such as ultrasound images captured during ultrasound examinations performed in the past. Hereinafter, an example of the configuration of a modified example of the medical image diagnosis device 100 for causing the display 340 to display information indicating the results of ultrasound examinations performed on the subject P in the past as information for supporting the examination will be described.

In the following description, the medical image diagnosis device 100 of the modified example is referred to as a "medical image diagnosis device 100*a*" and the medical image diagnosis system 1 to which the medical image diagnosis device 100*a* is applied is referred to as a "medical image diagnosis system 1*a*." In the following description, in the configuration and usage environment of the medical image diagnosis system 1*a* and the functional configuration of the components provided in the medical image diagnosis device 100*a*, parts similar to those of the configuration and usage environment of the medical image diagnosis system 1 and the functional configuration of components provided in the medical image diagnosis device 100 are denoted by the same reference signs and a detailed description thereof will be omitted.

Figure 6:
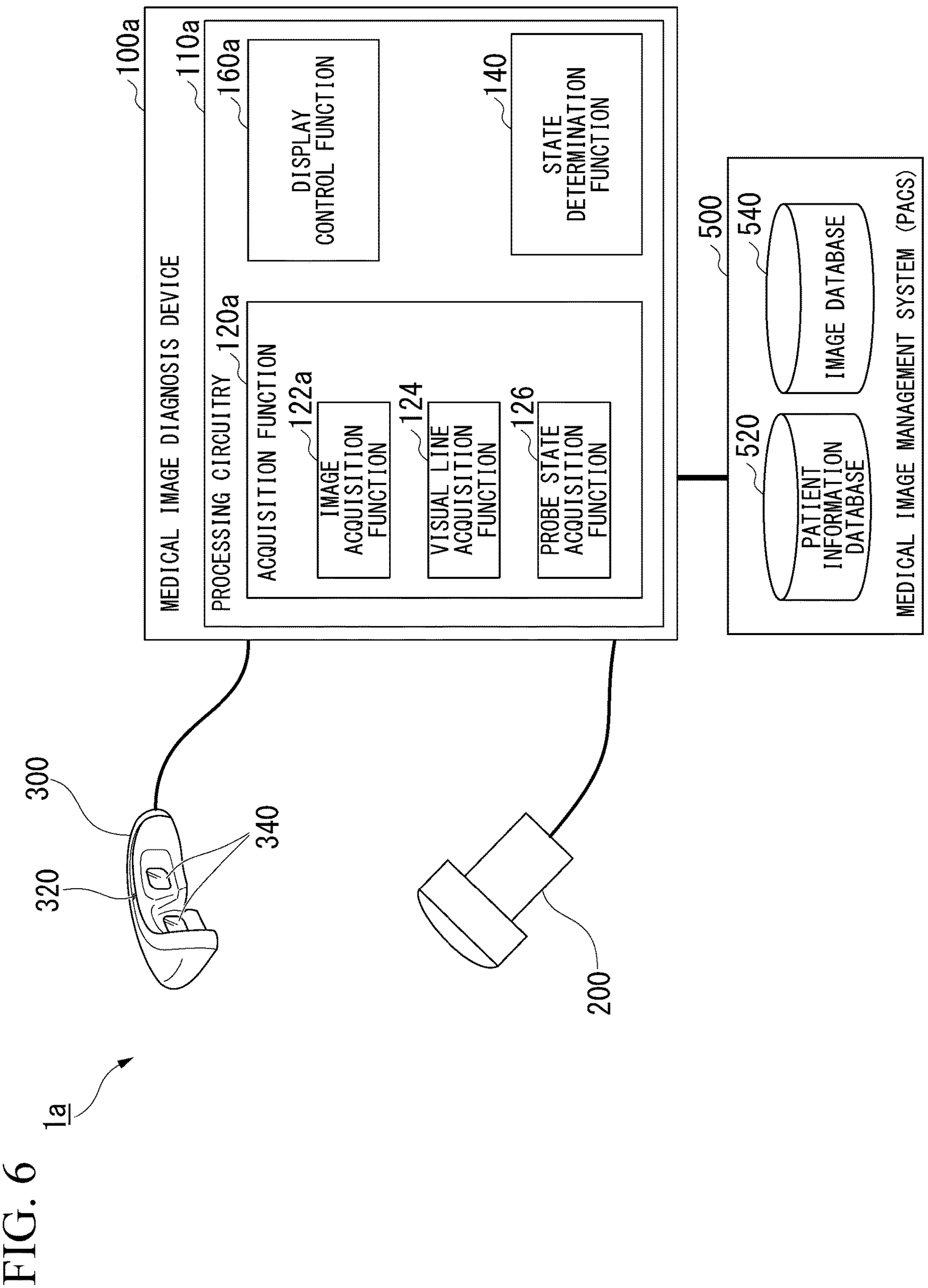
FIG. 6 is a diagram showing an example of a functional configuration of a modified example of the medical image diagnosis device according to the embodiment.

FIG. 6 is a diagram showing an example of a functional configuration of a modified example (the medical image diagnosis device 100*a*) of the medical image diagnosis device 100 according to the embodiment. The medical image diagnosis device 100*a* includes, for example, processing circuitry 110*a*. In FIG. 6, an example of the functional configuration of the processing circuitry 110*a* for implementing a function of displaying a display image on the display 340 provided in the HMD 300 in the medical image diagnosis device 100*a* is shown and the illustration of other components and functional configurations not related to the display of the display image are omitted. Furthermore, in FIG. 6, an example of the ultrasound probe 200 and the HMD 300 connected to the medical image diagnosis device 100*a* is also shown as the medical image diagnosis system 1*a*. In FIG. 6, an example of the configuration of the medical image diagnosis system 1*a* in a case where information of past ultrasound examinations to be displayed on the display 340 by the medical image diagnosis device 100*a* is stored in an external system is shown. More specifically, an example of a configuration in which a medical image management system (PACS) 500 is connected to the medical image diagnosis device 100*a* is shown. The medical image diagnosis device 100*a* and the medical image management system 500 may be connected, for example, by a network (not shown) such as a local area network (LAN) constructed within a hospital.

The medical image management system 500 is a database system that stores and manages various information about patients (including the subject P) who undergo treatment or examination in a hospital or the like where the medical image diagnosis system 1*a* is installed. The medical image management system 500 includes, for example, a patient information database 520 and an image database 540. The patient information database 520 stores various information about a large number of patients including the subject P, such as subject-specific information. The image database 540 stores information of images (including ultrasound images) of examinations performed on patients (including the subject P). Because the configuration, functions, and operations of the medical image management system 500 are similar to those of existing medical image management systems, detailed descriptions thereof will be omitted.

The processing circuitry 110*a*, for example, executes processing such as an acquisition function 120*a*, a state determination function 140, and a display control function 160*a*. The acquisition function 120*a*, for example, executes processes such as an image acquisition function 122*a*, a visual line acquisition function 124, and a probe state acquisition function 126. Like the processing circuitry 110 provided in the medical image diagnosis device 100, the processing circuitry 110*a* also implements these functions by, for example, a hardware processor executing a program (software) stored in a memory (not shown).

Like the acquisition function 120 within the processing circuitry 110 provided in the medical image diagnosis device 100, the acquisition function 120*a* is performed to acquire various information in ultrasound examinations. The acquisition function 120*a* is also an example of an "acquirer."

Like the image acquisition function 122 within the acquisition function 120, the image acquisition function 122*a* is performed to acquire the reflected wave signal output by the ultrasound probe 200 and the image signal transmitted (transferred) by the HMD 300 and output the acquired reflected wave signal and the acquired image signal to image processing circuitry (the image processing function) (not shown). Like the image acquisition function 122, the image acquisition function 122*a* may also be performed to generate an ultrasound image on the basis of the acquired reflected wave signal and generate a visual field image on the basis of the acquired image signal. In this case, like the image acquisition function 122, the image acquisition function 122*a* may also be performed to output the generated ultrasound image to the state determination function 140. As in the processing circuitry 110, in the processing circuitry 110*a*, an ultrasound image or a visual field image generated in the image processing circuitry (the image processing function) (not shown) or the image acquisition function 122 is output to the display control function 160*a*.

Furthermore, the image acquisition function 122*a* is performed to acquire information (hereinafter referred to as "past information") indicating results of ultrasound examinations performed on the subject P in the past stored in the medical image management system 500. In addition to ultrasound images saved in ultrasound examinations performed in the past, the past information includes, for example, information indicating the position and orientation of the ultrasound probe 200 when the saved ultrasound images were captured, i.e., the probe state information acquired in the probe state acquisition function 126, may be included. In this case, the probe state information may be associated with the ultrasound image and stored together with the ultrasound image. In the following description, in order to distinguish an ultrasound image saved in the past ultrasound examination and an ultrasound image captured during the current ultrasound examination, an ultrasound image saved in the ultrasound examination performed in the past is referred to as a "past image." Furthermore, probe state information indicating the position and orientation of the ultrasound probe 200 when past images were captured is referred to as an "imaging position." The image acquisition function 122*a* is performed to output past information (including past images and imaging positions) acquired from the medical image management system 500 to the display control function 160*a*.

Like the display control function 160 within the acquisition function 120, the display control function 160*a* is performed to control the display of a display image on the display 340 provided in the HMD 300. At this time, like the display control function 160, the display control function 160*a* is performed to dynamically change the ratio between the size of the ultrasound image to be superimposed as a display image and the size of the visual field image and cause the display 340 to display the image. Furthermore, when past information has been output in the image acquisition function 122*a* provided in the acquisition function 120*a*, the display control function 160*a* is performed to generate a display image including past information in addition to both or one of the ultrasound image and the visual field image and cause the display 340 to display a display image.

Figure 7:
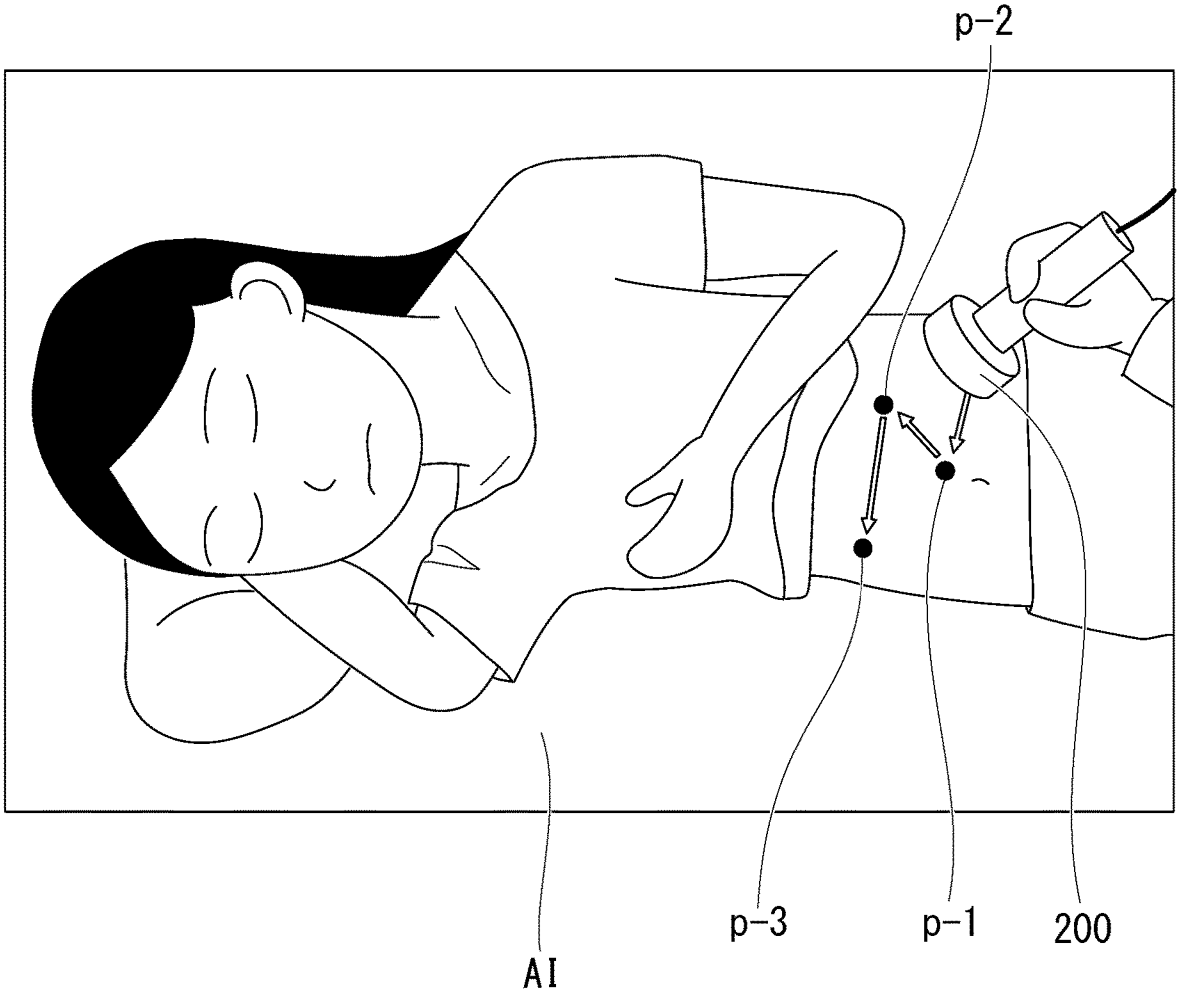
FIG. 7 is a diagram showing an example (part 1) of a display image displayed on a display device by a medical image diagnosis device of the modified example according to the embodiment.

Here, an example of the display image generated in the display control function 160*a* and displayed on the display 340 will be described. FIG. 7 is a diagram showing an example of a display image displayed on the display device (the display 340) by the medical image diagnosis device 100*a* according to the modified example of the embodiment. For ease of description, in FIG. 7, an example of a case where a display image in which information of an imaging position included in past information is shown in the current visual field image AI is displayed on the display 340 is shown.

The ultrasound probe 200 in the display image(=visual field image AI) shown in FIG. 7 indicates the current position of the ultrasound probe 200. The ultrasound probe 200 within the visual field image AI is imaged in the visual field image AI. Three imaging positions p (imaging positions p-1 to p-3) indicated by "circles" superimposed within the visual field image AI shown in FIG. 7 indicate positions of the ultrasound probe 200 when past images were captured during past (for example, previous) ultrasound examinations. Each of the imaging positions p is determined to be adapted to the current visual field image AI on the basis of the information of the imaging position included in the past information. Furthermore, the "arrow" superimposed within the visual field image AI shown in FIG. 7 indicates the order in which past images were captured in past ultrasound examinations by linking the imaging positions p. Thereby, the examiner D visually confirms the positions and order of ultrasound images confirmed and saved in past ultrasound examinations using the display image(=visual field image AI) shown in FIG. 7. The imaging positions p (the imaging positions p-1 to p-3) are examples of a "mark indicating an imaging position."

Although the display image(=visual field image AI) shown in FIG. 7 is an example when the ultrasound probe 200 is in contact with the body surface of the subject P, the imaging position p and arrows based on the past information as shown in FIG. 7 can be similarly shown even in a state in which the ultrasound probe 200 is away from the body surface of the subject P (the ultrasound probe 200 is in the air) in the visual field image AI.

Figure 8:
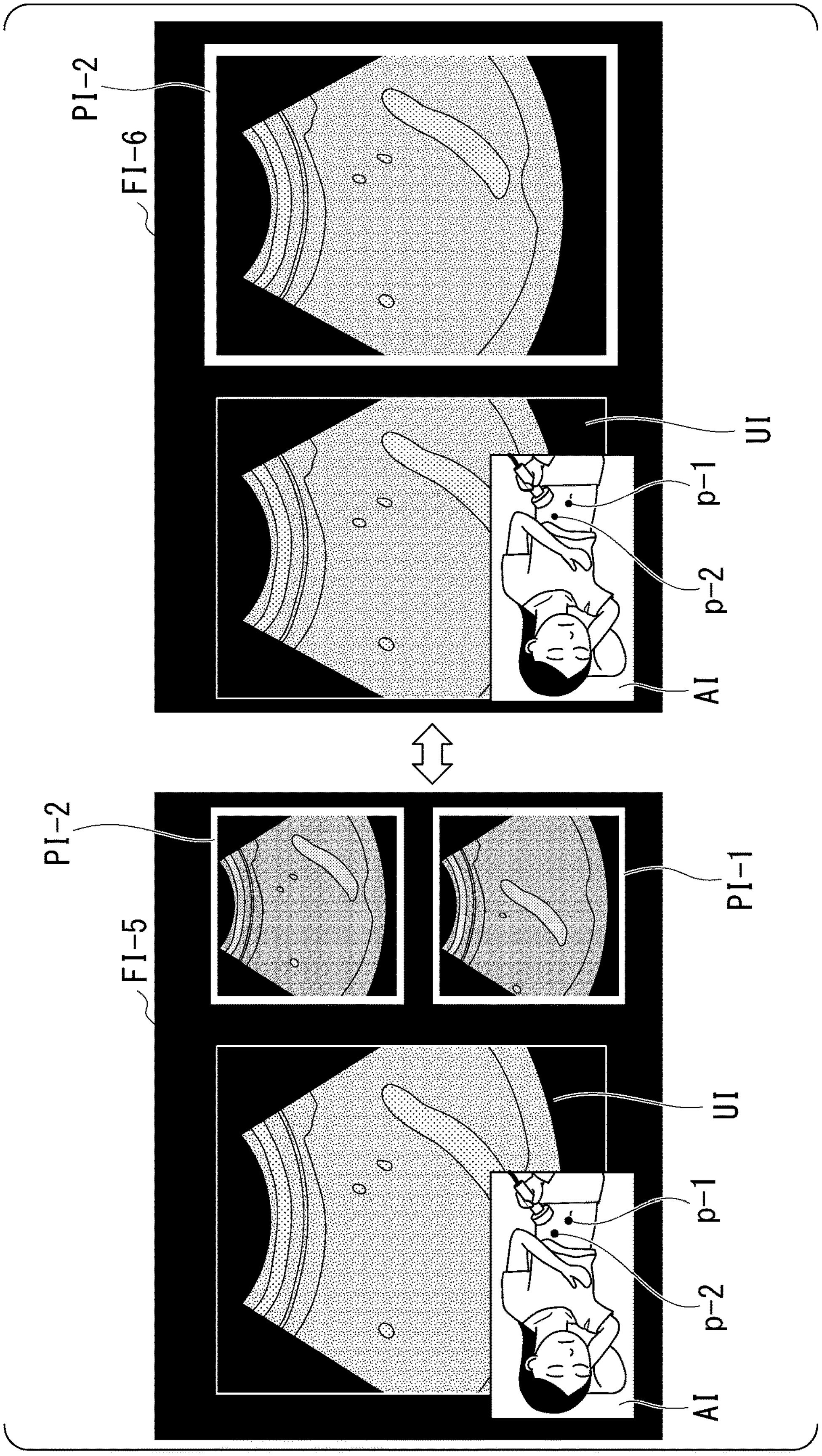
FIG. 8 is a diagram showing an example (part 2) of a display image displayed on the display device by the medical image diagnosis device of the modified example according to the embodiment.

Next, another example of a display image generated in the display control function 160*a* and displayed on the display 340 will be described. FIG. 8 is a diagram showing another example of a display image displayed on the display device (the display 340) by the medical image diagnosis device 100*a* according to the modified example of the embodiment. In FIG. 8, an example of a display image for displaying past information (past images and imaging position information included in past information) on the display 340 is shown in a case where both an ultrasound image and a visual field image are displayed on the display 340 when the ultrasound probe 200 is in contact with the body surface of the subject P.

In FIG. 8, the display image FI-5 is an example of a display image when the current position of the ultrasound probe 200 is away from the imaging position of the past image. At this time, like the display control function 160, the display control function 160*a* is performed to enlarge the ultrasound image display region where the current ultrasound image UI is displayed and reduce the visual field image display region where the current visual field image AI is displayed. Also, the display control function 160*a* is performed to generate the display image FI-5 in which "circles" of imaging positions p (here, two imaging positions p-1 and p-2) are shown within the visual field image AI and past images PI corresponding to the imaging positions p (here, a past image PI-1 corresponding to the imaging position p-1 and a past image PI-2 corresponding to the imaging position p-2) are shown within the ultrasound image UI. At this time, the display control function 160*a* is performed to generate the display image FI-5 in which each of the past image PI-1 and the past image PI-2 is superimposed on a display region smaller than the ultrasound image display region where the current ultrasound image UI is displayed. Also, the display control function 160*a* causes the display 340 to display the generated display image FI-5. Using the display image FI-5, the examiner D can scan the ultrasound probe 200 to search for a portion inside of the body of the subject P in the current ultrasound examination while confirming positions of the ultrasound probe 200 when ultrasound images (past images) were captured during past ultrasound examinations and ultrasound images (past images) confirmed at the positions and saved together with a current visual field image AI and a current ultrasound image UI.

In FIG. 8, the display image FI-6 is an example of a display image when the current position of the ultrasound probe 200 is a position equivalent to the imaging position of the past image (a position close to or identical to the imaging position of the past image). At this time as well, the display control function 160*a* is performed to enlarge the ultrasound image display region where the current ultrasound image UI is displayed and reduce the visual field image display region where the current visual field image AI is displayed. Also, the display control function 160*a* is performed to show "circles" at the imaging positions p (the imaging positions p-1 and p-2) in the visual field image AI as in the display image FI-5. Because the current position of the ultrasound probe 200 is equivalent to the imaging position of the past image, the display control function 160*a* is performed to generate the display image FI-6 in which the past image PI corresponding to the equivalent imaging position p (here, the past image PI-2 corresponding to the imaging position p-2) is superimposed on a display region larger than the display image FI-5 within the ultrasound image UI. Here, the display control function 160*a* may be performed to make the size of the display region of the past image PI-2 to be superimposed smaller than or equal to the size of the ultrasound image display region where the current ultrasound image UI is displayed. Also, the display control function 160*a* causes the display 340 to display the generated display image FI-6. Using the display image FI-6, the examiner D can confirm the current ultrasound image UI in detail while comparing it with ultrasound images (past images) captured at equivalent positions in past ultrasound examinations and make a clinical diagnosis (determination).

With this configuration, in the medical image diagnosis device 100*a*, like the medical image diagnosis device 100, both the current visual field image captured by the camera 320 provided in the HMD 300 and the current ultrasound image captured by the ultrasound probe 200 are displayed on the display 340 provided in the HMD 300 and sizes of the visual field image and the ultrasound image displayed on the HMD 300 are dynamically changed in accordance with an imaging state during an examination. Thereby, as in the case where the ultrasound examination is performed using the medical image diagnosis device 100, the examiner D who performs an ultrasound examination using the medical image diagnosis device 100*a* can simultaneously perform the confirmation of the state of the external appearance of the subject P within the visual field range (the confirmation of the visual field image) and the confirmation of the state of the inside of the body of the subject P (the confirmation of the ultrasound image) through high-resolution images without taking an unreasonable orientation. Furthermore, in the medical image diagnosis device 100*a*, results of ultrasound examinations performed in the past on the same subject P (including a past image and an imaging position) are displayed on the display 340 together with the current visual field image and the current ultrasound image. Thereby, the examiner D who performs an ultrasound examination using the medical image diagnosis device 100*a* can smoothly perform the current ultrasound examination while confirming the results of past ultrasound examinations.

Although a case where the ultrasound probe 200 is used in contact with or in proximity to the body surface of the subject P has been described in the above-described configuration of the medical image diagnosis system 1*a*, it is similar to the medical image diagnosis device 100 even if the ultrasound probe 200 is inside of the body of the subject P. Furthermore, in the case where the operation image is displayed on the display 340 together with the visual field image and the ultrasound image in the medical image diagnosis device 100*a*, the medical image diagnosis device 100*a* is similar to the medical image diagnosis device 100. Therefore, a detailed description of the configuration, processing, examples of display images, and the like in these cases will be omitted.

As described above, in the medical image diagnosis device of the embodiment, the display device attached to the head of the examiner is allowed to display both the visual field image of the range of the visual field of the examiner captured by the imaging device provided in the display device attached to the head of the examiner and the ultrasound image captured by the ultrasound probe. Thereby, an examiner who performs an ultrasound examination using the medical image diagnosis device of the embodiment can simultaneously confirm the visual field image and the ultrasound image without taking an unreasonable orientation using the display device attached to the head in a state in which the ultrasound image is not projected onto the body surface of the subject as in the conventional ultrasound examination. Furthermore, the medical image diagnosis device of the embodiment dynamically changes the sizes of the visual field image and the ultrasound image to be displayed on the display device attached to the head of the examiner in accordance with the imaging state during the ultrasound examination. Thereby, an examiner who performs an ultrasound examination using the medical image diagnosis device of the embodiment can confirm the state of the external appearance of the subject using a high-resolution visual field image and the state of the inside of the body of the subject using a high-resolution ultrasound image. Thereby, an examiner who performs an ultrasound examination using the medical image diagnosis device of the embodiment can make a more accurate clinical diagnosis (determination). In other words, the medical image diagnosis device of the embodiment does not impose a physical burden on the examiner unlike a conventional ultrasound examination, i.e., it is possible to smoothly confirm both the state of the external appearance of the subject and the state of the inside of the body of the subject in a state in which the physical load on the examiner is reduced as compared with the conventional ultrasound examination.

In the above-described embodiment, a configuration in which the HMD 300 connected to the medical image diagnosis device 100 or the medical image diagnosis device 100*a* includes the camera 320 and the camera 320 images a range of the visual field of the examiner D has been described. However, the HMD 300 connected to the medical image diagnosis device 100 or the medical image diagnosis device 100*a* may have a configuration including at least a display 340, i.e., a configuration in which the camera 320 is omitted. In this case, the range of the visual field of the examiner D may be imaged by, for example, any imaging device capable of imaging the range of the visual field of the examiner D such as another imaging device attached to the head of the examiner D simultaneously with the HMD 300 only including the display 340 or an imaging device installed in an examination room where the ultrasound examination of the subject P is performed. It is only necessary for the functional configuration, operation, processing, and the like of the medical image diagnosis device 100 or the medical image diagnosis device 100*a* in this case to be equivalent to the functional configuration, operation, processing, and the like of the medical image diagnosis device 100 or the medical image diagnosis device 100*a* of the above-described embodiment and this is easily conceivable. Therefore, a detailed description of the functional configuration, operation, processing, and the like of the medical image diagnosis device 100 or the medical image diagnosis device 100*a* in this case will be omitted.

In the above-described embodiment, the case where a component that is connected to the medical image diagnosis device 100 or the medical image diagnosis device 100*a* and allows both the visual field image and the ultrasound image to be within the visual field of the examiner D at the same time is the HMD 300, which is a video transmission type head mounted display, has been described. However, the component for allowing both the visual field image and the ultrasound image to be within the visual field of the examiner D at the same time is any device, instrument, or system as long as it is a component capable of allowing both the visual field image and the ultrasound image to be within the visual field of the examiner D at the same time. For example, an optically transmissive head-mounted display may be used instead of the HMD 300 as long as it can dynamically change the ratio between the size of the region of the real image (corresponding to the visual field image) of the visual field of the examiner D that is optically transmitted and the size of the ultrasound image display region of the ultrasound image.

According to at least one embodiment described above, processing circuitry is provided to acquire at least a reflected wave signal obtained by reflecting an ultrasound signal detected by an ultrasound probe (200) and transmitted to a subject (P) within a body of the subject and an image signal including an external appearance of the subject captured by an imaging device (320) (120); control a process of displaying an ultrasound image (UI) based on the reflected wave signal and a visual field image (AI) based on the image signal on a display device (340) attached to a head of an examiner (D) (160); and determine whether or not a state is an imaging state in which the ultrasound probe detects the reflected wave signal and the inside of the body of the subject is imaged (140), wherein the processing circuitry dynamically changes the ratio between the size of an ultrasound image display region where the ultrasound image is displayed on the display device and the size of a visual field image display region where the visual field image is displayed on the display device on the basis of an imaging state determination result, whereby a medical image diagnosis device (100) can allow the examiner to smoothly perform the confirmation of the state of the subject and the confirmation of the diagnosis image (the ultrasound image).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The following appendixes are disclosed as aspects and selective features of the invention in relation to the above embodiment.

(Appendix 1)

A medical image diagnosis device including:

processing circuitry configured to acquire at least a reflected wave signal obtained by reflecting an ultrasound signal detected by an ultrasound probe and transmitted to a subject within a body of the subject and an image signal including an external appearance of the subject captured by an imaging device;

control a process of displaying an ultrasound image based on the reflected wave signal and a visual field image based on the image signal on a display device attached to a head of an examiner; and determine whether or not a state is an imaging state in which the ultrasound probe detects the reflected wave signal and the inside of the body of the subject is imaged, wherein the processing circuitry dynamically changes the ratio between the size of an ultrasound image display region where the ultrasound image is displayed on the display device and the size of a visual field image display region where the visual field image is displayed on the display device based on an imaging state determination result.

(Appendix 2)

The processing circuitry may determine the imaging state based on the reflected wave signal.

(Appendix 3)

The processing circuitry may make the size of the visual field image display region greater than the size of the ultrasound image display region when the imaging state determination result is a first state in which the inside of the body of the subject is not imaged and may make the size of the ultrasound image display region greater than the size of the visual field image display region when the imaging state determination result is a second state in which the inside of the body of the subject is imaged.

(Appendix 4)

The processing circuitry may cause the display device to perform a display process in which the ultrasound image display region overlaps a partial region within the visual field image display region and the ultrasound image is allowed to be superimposed on the visual field image when the imaging state determination result is the first state, and may cause the display device to perform a display process in which the visual field image display region overlaps a partial region within the ultrasound image display region and the visual field image is allowed to be superimposed on the ultrasound image when the imaging state determination result is the second state.

(Appendix 5)

The processing circuitry may further acquire a position of a visual line of the examiner toward the inside of an image display region in the display device, determines a gaze state of the examiner based on the position of the visual line, and dynamically changes the ratio between the size of the ultrasound image display region and the size of the visual field image display region based on a gaze state determination result.

(Appendix 6)

The processing circuitry may further acquire a detection position of the reflected wave signal in the ultrasound probe, determine a detection state of the ultrasound probe based on the detection position, and dynamically change the ratio between the size of the ultrasound image display region and the size of the visual field image display region based on a detection state determination result.

(Appendix 7)

The processing circuitry may further acquire past information from a past examination performed for the subject, and may control a process of displaying the past information on the display device.

(Appendix 8)

The past information may include a past image, which is the ultrasound image obtained in the past examination for the subject, and an imaging position, which is a position where the reflected wave signal was detected by the ultrasound probe when the past image was captured, when the imaging state determination result is a state in which the inside of the body of the subject is being imaged, the processing circuitry may cause at least one past image to be displayed in a display region smaller than the ultrasound image display region together with the ultrasound image and the visual field image, and may cause a mark indicating the imaging position to be superimposed and displayed on the visual field image.

(Appendix 9)

The processing circuitry may further acquire a detection position of the reflected wave signal in the ultrasound probe and dynamically change the size of a display region of the past image in accordance with a distance between the detection position and the imaging position.

(Appendix 10)

A medical image diagnosis system including:

an ultrasound probe configured to detect and output a reflected wave signal obtained by reflecting an ultrasound signal transmitted to a subject within a body of the subject;

a head-mounted display attached to a head of an examiner and including at least an imaging device configured to output an image signal obtained by capturing an image including the external appearance of the subject and a display device configured to display an image input to be presented to the examiner; and processing circuitry configured to acquire at least the reflected wave signal and the image signal, control a process of displaying an ultrasound image based on the reflected wave signal and a visual field image based on the image signal on the display device, and determine whether or not a state is an imaging state in which the ultrasound probe detects the reflected wave signal and the inside of the body of the subject is imaged, wherein the processing circuitry dynamically changes the ratio between the size of an ultrasound image display region where the ultrasound image is displayed on the display device and the size of a visual field image display region where the visual field image is displayed on the display device based on an imaging state determination result.

What is claimed is:

1. A medical image diagnosis device comprising:

processing circuitry configured to:

acquire at least a reflected wave signal obtained by reflecting an ultrasound signal detected by an ultrasound probe and transmitted to a subject within a body of the subject and an image signal including an external appearance of the subject captured by a camera;

control a process of displaying an ultrasound image based on the reflected wave signal and a visual field image based on the image signal on a display device attached to a head of an examiner;

determine whether a state is one of (a) a first state in which the ultrasound probe is away from a body surface of the subject and an inside of the body of the subject is not being imaged, or (b) a second state in which the ultrasound probe is in contact with or in proximity to the body surface of the subject and the inside of the body of the subject is being imaged;

dynamically and automatically change a ratio between a size of an ultrasound image display region where the ultrasound image is displayed on the display device and a size of a visual field image display region where the visual field image is displayed on the display device based on a determination result of whether the state is the first state or the second state; and dynamically and automatically switch displaying on the display device between displaying of a first display image in response to the determination result indicating the first state and displaying of a second display image in response to the determination result indicating the second state, the first display image being an image in which the size of the visual field image display region is greater than the size of the ultrasound image display region in the first state, the second display image being an image in which the size of the ultrasound image display region is greater than the size of the visual field image display region in the second state.

2. The medical image diagnosis device according to claim 1, wherein the processing circuitry is further configured to determine the state based on the reflected wave signal.

3. The medical image diagnosis device according to claim 1, wherein the processing circuitry is further configured to:

cause the display device to perform a display process in which the ultrasound image display region overlaps a partial region within the visual field image display region in the first state; and cause the display device to perform a display process in which the visual field image display region overlaps a partial region within the ultrasound image display region in the second state.

4. The medical image diagnosis device according to claim 1, wherein the processing circuitry is further configured to:

acquire, from a visual line sensor included in the display device, information indicating a position of a visual line of the examiner toward the inside of an image display region in the display device;

determine a gaze state of the examiner based on the information indicating the position of the visual line; and dynamically change the ratio between the size of the ultrasound image display region and the size of the visual field image display region based on a determination result of the gaze state.

5. The medical image diagnosis device according to claim 1, wherein the processing circuitry is further configured to:

acquire position information indicating a position of the ultrasound probe;

determine a detection state of the ultrasound probe based on the position information; and determine the state based on the determined detection state.

6. The medical image diagnosis device according to claim 1, wherein the processing circuitry is further configured to:

acquire past information from a past examination performed for the subject; and control a process of displaying the past information on the display device.

7. The medical image diagnosis device according to claim 6, wherein the past information includes a past image, which is the ultrasound image obtained in the past examination for the subject, and an imaging position, which is a position where the reflected wave signal was detected by the ultrasound probe when the past image was captured, and wherein, in the second state, the processing circuitry is further configured to:

cause the past image to be displayed in a display region smaller than the ultrasound image display region together with the ultrasound image and the visual field image; and cause a mark indicating the imaging position to be superimposed and displayed on the visual field image.

8. The medical image diagnosis device according to claim 7, wherein the processing circuitry is further configured to:

acquire position information indicating a position of the ultrasound probe; and dynamically change a size of a display region of the past image in accordance with a distance between the position of the ultrasound probe indicated by the position information and the imaging position.

9. A medical image diagnosis system comprising:

an ultrasound probe configured to detect and output a reflected wave signal obtained by reflecting an ultrasound signal transmitted to a subject within a body of the subject;

a head-mounted display configured to be attached to a head of an examiner and including at least a camera configured to output an image signal obtained by capturing an image including the external appearance of the subject and a display device configured to display an image input to be presented to the examiner; and processing circuitry configured to:

acquire at least the reflected wave signal and the image signal, control a process of displaying an ultrasound image based on the reflected wave signal and a visual field image based on the image signal on the display device, and determine whether a state is one of (a) a first state in which the ultrasound probe is away from a body surface of the subject and an inside of the body of the subject is not being imaged, or (b) a second state in which the ultrasound probe is in contact with or in proximity to the body surface of the subject and the inside of the body of the subject is being imaged;

dynamically and automatically change a ratio between a size of an ultrasound image display region where the ultrasound image is displayed on the display device and a size of a visual field image display region where the visual field image is displayed on the display device based on a determination result of whether the state is the first state or the second state; and dynamically and automatically switch displaying on the display device between displaying of a first display image in response to the determination result indicating the first state and displaying of a second display image in response to the determination result indicating the second state, the first display image being an image in which the size of the visual field image display region is greater than the size of the ultrasound image display region in the first state, the second display image being an image in which the size of the ultrasound image display region is greater than the size of the visual field image display region in the second state.

* * * * *